United States Patent
Lee et al.

(10) Patent No.: US 10,143,953 B1
(45) Date of Patent: Dec. 4, 2018

(54) AROMA-DISPENSING HVAC FILTER

(71) Applicants: Efrem Lee, Waukegan, IL (US); Penelope Lee, Waukegan, IL (US)

(72) Inventors: Efrem Lee, Waukegan, IL (US); Penelope Lee, Waukegan, IL (US)

( * ) Notice: Subject to any disclaimer, the term of this patent is extended or adjusted under 35 U.S.C. 154(b) by 114 days.

(21) Appl. No.: 15/407,513

(22) Filed: Jan. 17, 2017

(51) Int. Cl.
*A61L 9/12* (2006.01)
*B01D 46/00* (2006.01)
*B01D 46/10* (2006.01)
*F24F 7/06* (2006.01)

(52) U.S. Cl.
CPC ......... *B01D 46/0038* (2013.01); *A61L 9/12* (2013.01); *B01D 46/0005* (2013.01); *B01D 46/0057* (2013.01); *B01D 46/10* (2013.01); *A61L 2209/14* (2013.01); *A61L 2209/16* (2013.01); *B01D 2279/35* (2013.01); *F24F 7/06* (2013.01)

(58) Field of Classification Search
CPC ......... B01D 46/0038; B01D 46/0005; B01D 46/0057; B01D 46/10; B01D 2279/35; A61L 9/12; A61L 2209/14; A61L 2209/16; F24F 7/06
USPC ...... 96/222; 55/493, 506, DIG. 35; 422/123; 261/DIG. 88
See application file for complete search history.

(56) References Cited

U.S. PATENT DOCUMENTS

| | | | |
|---|---|---|---|
| 2,057,568 A * | 10/1936 | Gerard ............... | B01D 46/10 55/481 |
| 2,575,499 A * | 11/1951 | Manow ............... | B01D 46/10 454/284 |
| 3,280,984 A * | 10/1966 | Sexton ............... | B01D 46/10 210/485 |
| 3,724,671 A * | 4/1973 | Tate .................. | B01D 46/10 210/484 |
| 4,604,114 A | 8/1986 | Ward | |
| 4,737,174 A * | 4/1988 | Pontius ............... | B01D 46/12 55/491 |
| 4,801,316 A * | 1/1989 | Schroeder ............ | B01D 46/10 55/385.1 |
| 4,875,912 A | 10/1989 | Fulmer | |
| 5,571,300 A * | 11/1996 | Stemmer ............. | B01D 46/10 55/493 |
| 5,947,815 A * | 9/1999 | Danforth ............. | F24F 13/28 454/289 |
| 6,257,976 B1 * | 7/2001 | Richardson, III ..... | F24F 13/082 422/124 |
| 6,630,233 B1 | 10/2003 | Levandowski | |
| D679,792 S | 4/2013 | Hollingsworth | |
| 9,132,373 B2 * | 9/2015 | Loggins ............. | B01D 46/0005 |
| 2002/0157540 A1 * | 10/2002 | Lynn ................. | A45D 20/12 96/222 |
| 2009/0078121 A1 * | 3/2009 | Hepburn ............. | A61L 9/16 96/222 |
| 2010/0186594 A1 | 7/2010 | Gelo | |
| 2012/0234175 A1 | 9/2012 | Sanchez | |
| 2014/0041525 A1 | 2/2014 | Morrow | |

FOREIGN PATENT DOCUMENTS

CA 2852134 A1 11/2014

* cited by examiner

*Primary Examiner* — Frank M Lawrence, Jr.
(74) *Attorney, Agent, or Firm* — Kyle A. Fletcher, Esq.

(57) ABSTRACT

The aroma-dispensing HVAC filter is a scented air filter capable of diffusing a pleasant odor throughout a building. The filter media is enclosed in an easily-opened, protective holder.

14 Claims, 4 Drawing Sheets

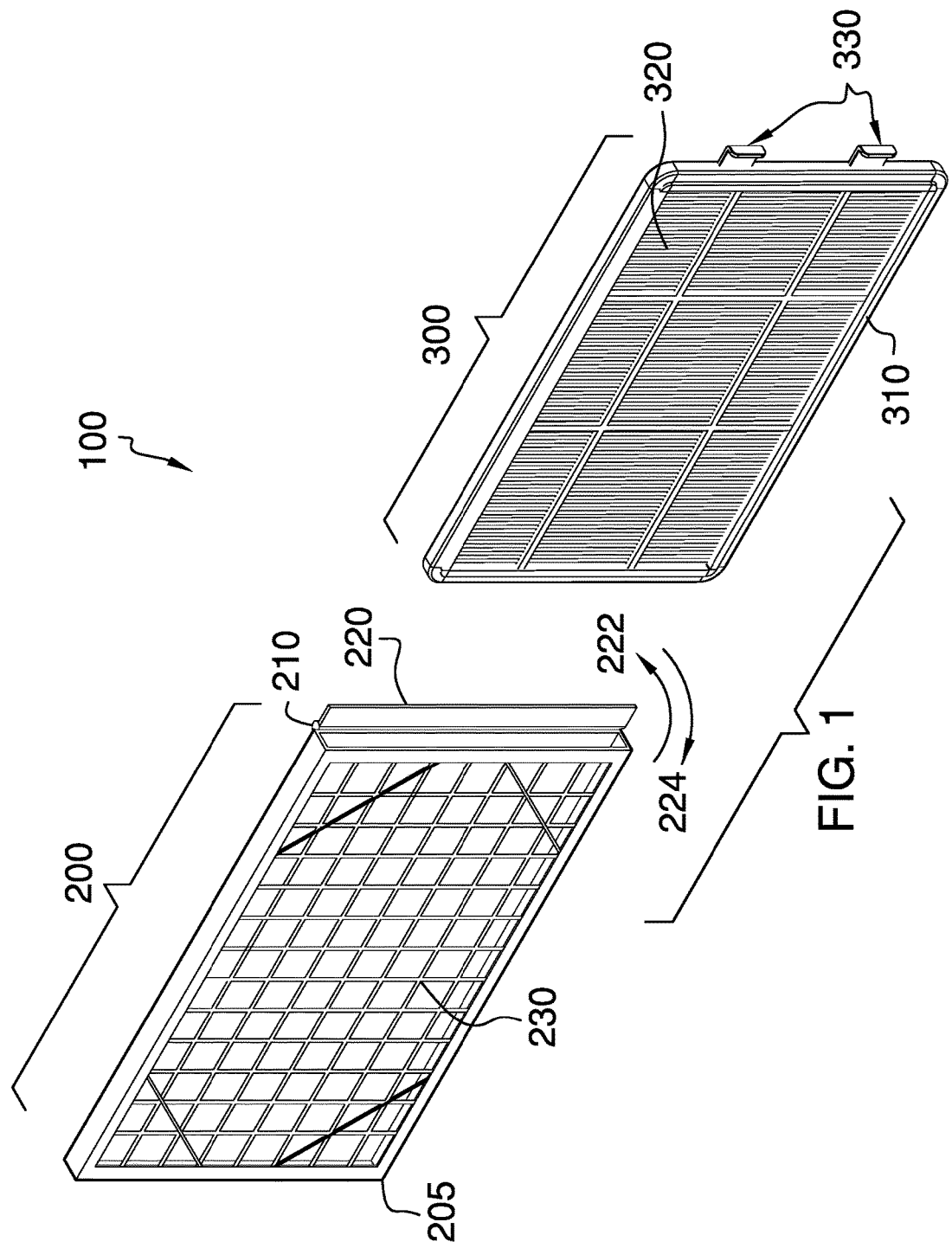

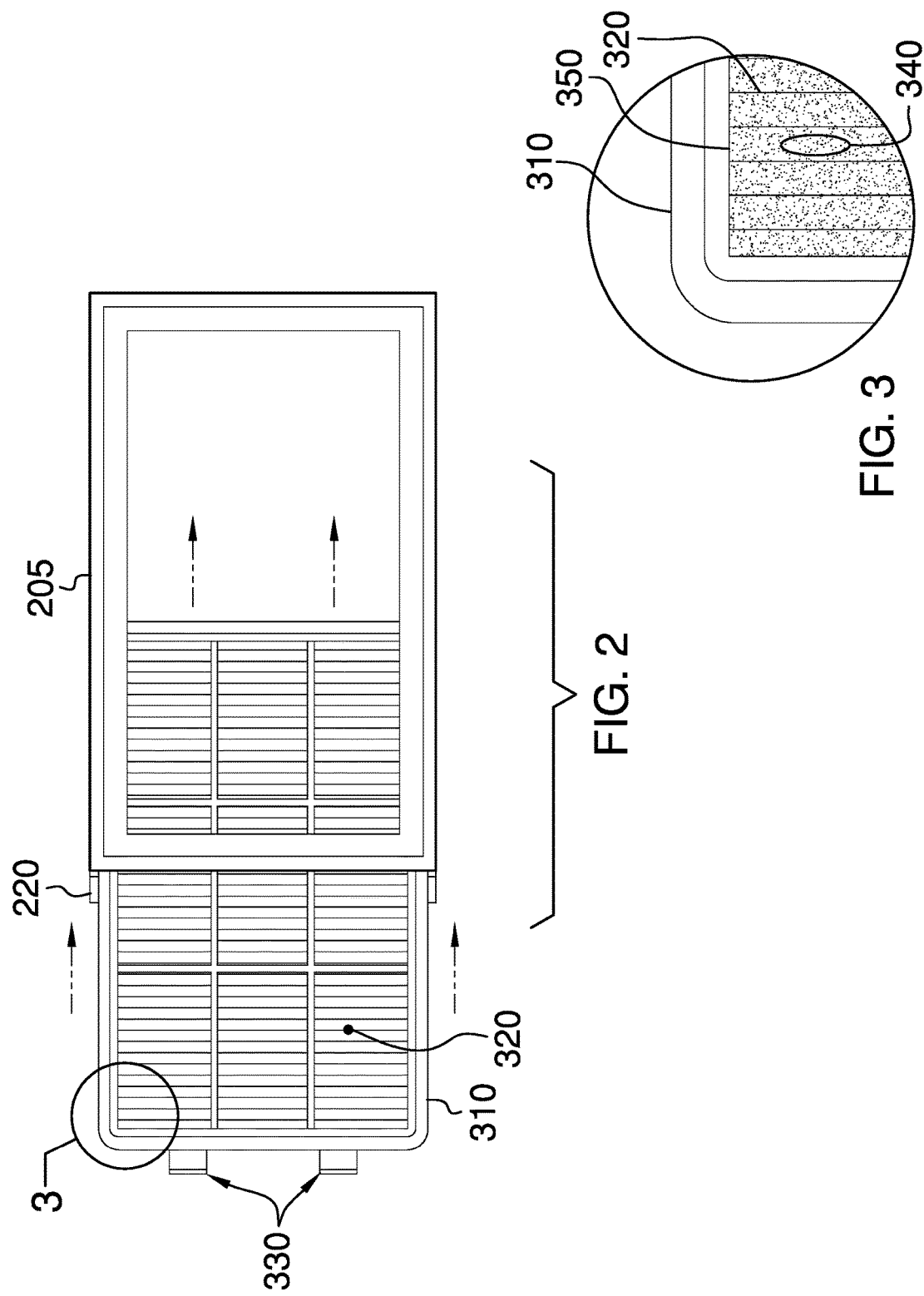

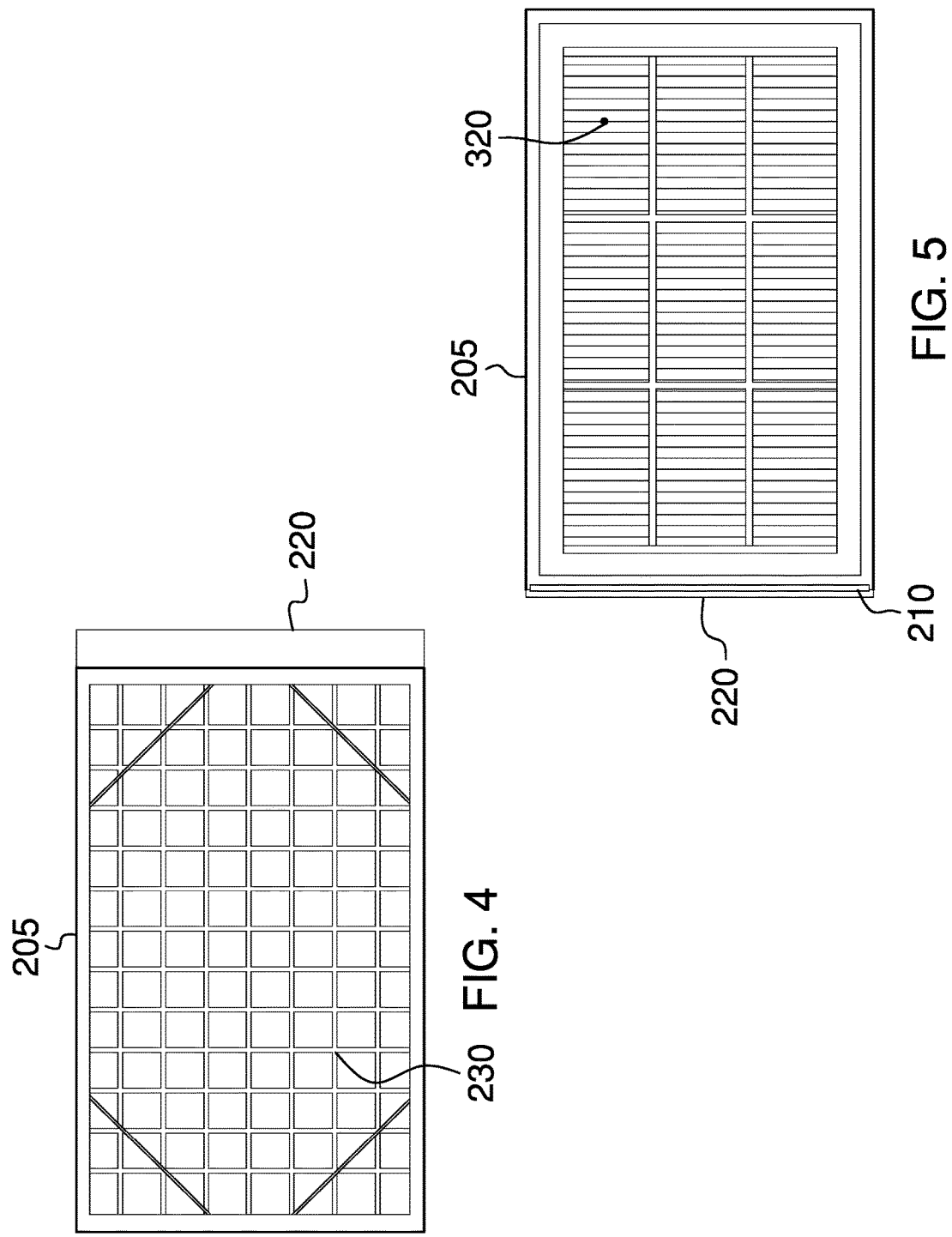

AROMA-DISPENSING HVAC FILTER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of heating, ventilation, and air conditioning systems (HVAC), more specifically, a replaceable air filter with aromatic properties.

SUMMARY OF INVENTION

The aroma-dispensing HVAC filter is a scented air filter capable of diffusing a pleasant odor throughout a building. The filter media is enclosed in an easily-opened, protective holder.

An object of the invention is to provide an aromatic air filter capable of diffusing a scent throughout a building.

A further object of the invention is to allow the aromatic air to be easily replaced.

These together with additional objects, features and advantages of the aroma-dispensing HVAC filter will be readily following detailed description of the presently preferred, but nonetheless illustrative, embodiments when taken in conjunction with the accompanying drawings.

In this respect, before explaining the current embodiments of the aroma-dispensing HVAC filter in detail, it is to be understood that the aroma-dispensing HVAC filter is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the aroma-dispensing HVAC filter.

It is therefore important that the claims be regarded as including such equivalent construction insofar as they do not depart from the spirit and scope of the aroma-dispensing HVAC filter. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an serve to explain the principles of the invention. They are meant to be exemplary illustrations provided to enable persons skilled in the art to practice the disclosure and are not intended to limit the scope of the appended claims.

FIG. 1 is a perspective view of an embodiment of the disclosure.

FIG. 2 is a front view of an embodiment of the disclosure illustrating the replaceable filter being installed in the filter holder.

FIG. 3 is a detail view of an embodiment of the disclosure in the area indicated in FIG. 2.

FIG. 4 is a front view of an embodiment of the disclosure illustrating an empty filter holder.

FIG. 5 is a rear view of an embodiment of the disclosure illustrating the filter holder with a replaceable filter installed.

DETAILED DESCRIPTION OF THE EMBODIMENT

Figure 6:
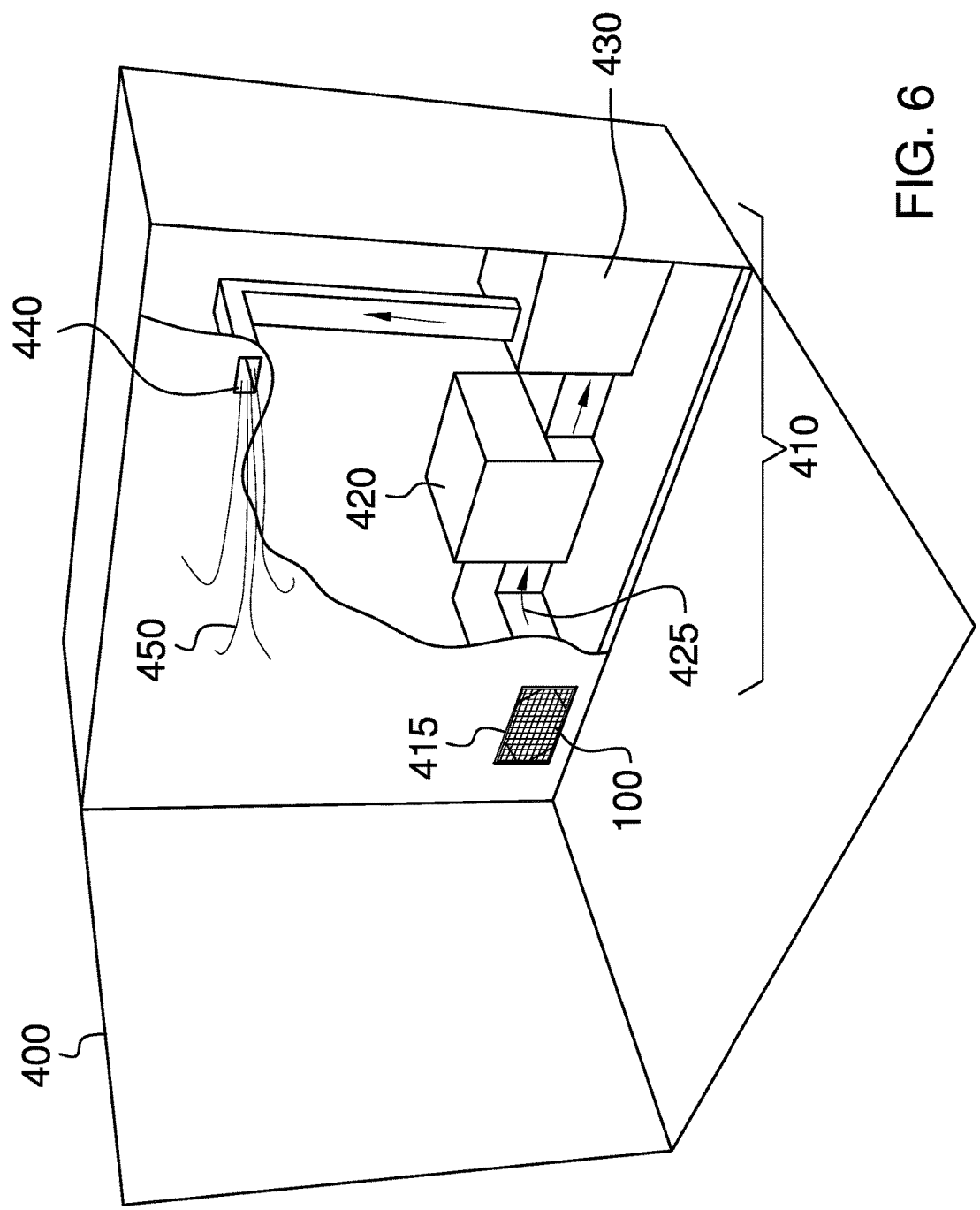
FIG. 6 is a perspective, cut-away view of a portion of a building illustrating the use of an embodiment of the disclosure.

The following detailed description is merely exemplary in nature and is not intended to limit the described embodiments of herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 6.

The aroma-dispensing HVAC filter 100 (hereinafter invention) comprises a filter holder 200 and a replaceable filter 300. The filter holder 200 functions as a carrier and protective cover for the replaceable filter 300. The replaceable filter 300 is inserted into the filter holder 200 and then the filter holder 200 is installed at an intake 415 of a ventilation system 410 of a building 400.

The filter holder 200 comprises a filter holder frame 205, a hinge 210, a flap 220, and a protective screen 230. The flap 205 using the hinge 210. In some embodiments, the hinge 210 may be a piano hinge. The flap 220 is moved to a first flap position 222 to insert the replaceable filter 300 into the filter holder 200. The flap 220 is then moved to a second flap position 224 to retain the replaceable filter 300 within the filter holder frame 205. The protective screen 230 comprises a screen, mesh, fence, or other arrangement of support material covering the front side of the filter holder 200, allowing air to flow through the replaceable filter 300, and intended to support the replaceable filter 300 against an air flow 425 and to protect the replaceable filter 300 from damage. In some embodiments the protective screen 230 may cover both sides of the filter holder 200.

The replaceable filter 300 comprises a filter frame 310, filter media 320, and at least one handle 330. The filter frame 310 is sized to fit snugly within the filter holder frame 205. The at least one handle 330 is attached to one side of the filter frame 310 to assist in removal of the replaceable filter 300 from the filter holder 200. The filter media 320 allows air to flow through the filter media 320, but captures much of the particulate matter being carried by the air, thus filtering the particulates out of the air flow 425. Non-limiting examples of materials suitable for use as the filter media 320 includes and corrugated aluminum. In some embodiments, the filter media 320 may have high-efficiency particulate air (HEPA) filtering properties. The filter media 320 is shaped to fit within the filter frame 310 and the filter media 320 is bonded to an inside edge 350 of the filter frame 310.

The replaceable filter 300 is infused, coated, or otherwise carries a fragrance agent 340 such that when the invention 100 is placed at the intake 415 of a ventilation system 410 in the building 400, the invention 100 infuses a fragrant odor 450 into the air flow 425 passing through the invention 100. The fragrance agent 340 may originally be applied to the replaceable filter 300 in the form of a liquid, an oil, a gel, a residue, adhesive particles, or some other form of scent delivery. Depending upon the fragrance agent 340, the fragrance agent 340 may dry on the replaceable filter 300 or it may remain wet or oily. In the later case, the replaceable filter 300 may be delivered to the user wrapped in plastic until ready to install.

In use, the flap 220 of the filter holder 200 is moved to the first flap position, and the replaceable filter 300 is inserted into the filter holder 200. The flap 220 is then moved to the second flap position 224, and the filter holder 200 is inserted into the intake 415 of the ventilation system 410 within the building 400. A blower 420 within the ventilation pass through the replaceable filter 300. In the process of passing through the replaceable filter 300 particulates (not shown) are caught by the filter media 320 and the fragrance agent 340 infuses a scent into the air flow 425.

The air may pass through a heating or cooling element 430 of the ventilation system 410, and eventually reaches the one or more air vents 440 where the fragrant odor 450 is distributed into the building 400. When the replaceable filter 300 has been in use for several months it may be replaced by removing the filter holder 200 from the intake 415 of the ventilation system 410, moving the flap 220 to the first flap position 222, pulling on the at least one handle 330 to withdraw the replaceable filter 300 from the filter holder 200, and then, with a new or cleaned filter, installing the replaceable filter 300 as described above. In some embodiments, the replaceable filter 300 may be disposable after use. In some embodiments the replaceable filter 300 may be washed and dried or otherwise cleaned and then reused. In certain embodiments it may be possible to replenish the fragrance agent 340 by applying the fragrance agent 340 to the filter media 320. As a non-limiting example, it may be possible to spray a scented solution (not shown) onto the filter media 320 to restore the fragrance agent 340.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An aroma-dispensing HVAC filter comprising:
a filter holder and a replaceable filter;
wherein the filter holder functions as a carrier and protective cover for the replaceable filter;
wherein the replaceable filter carries a fragrance agent;
wherein the replaceable filter is inserted into the filter holder and then the filter holder is configured to be installed at an intake of a ventilation system of a building;
wherein the filter holder comprises a filter holder frame, a hinge, a flap, and two protective screens covering opposite sides of the filter;
wherein the flap is hingedly connected to an edge of the filter holder frame using the hinge.

2. The aroma-dispensing HVAC filter according to claim 1 wherein the hinge is a piano hinge.

3. The aroma-dispensing HVAC filter according to claim 1 wherein the flap is moved to a first flap position to open the filter holder for insertion of the replaceable filter into the filter holder.

4. The aroma-dispensing HVAC filter according to claim 3 wherein the flap is moved to a second flap position to retain the replaceable filter within the filter holder frame.

5. The aroma-dispensing HVAC filter according to claim 4 wherein the protective screens comprise a covering for the front side of the filter holder;
wherein the covering allows air to flow through the replaceable filter;
wherein the covering supports the replaceable filter against an air flow and protects the replaceable filter from damage.

6. The aroma-dispensing HVAC filter according to claim 5 wherein the replaceable filter comprises a filter frame, a filter media, and at least one handle;
wherein the filter frame is sized to fit within the filter holder frame.

7. The aroma-dispensing HVAC filter according to claim 6 wherein the at least one handle is attached to one side of the filter frame to assist in removal of the replaceable filter from the filter holder.

8. The aroma-dispensing HVAC filter according to claim 7 wherein the filter media allows air to flow through the filter media and captures particulate matter being carried by the air.

9. The aroma-dispensing HVAC filter according to claim 8 wherein the filter media comprises a high-efficiency particulate air filter.

10. The aroma-dispensing HVAC filter according to claim 9 wherein the filter media is shaped to fit within the filter frame and the filter media is bonded to an inside edge of the filter frame.

11. The aroma-dispensing HVAC filter according to claim 10 wherein the replaceable filter carries the fragrance agent;
wherein placing the aroma-dispensing HVAC filter at the intake of the ventilation system in the building infuses a fragrant odor into the air flow passing through the aroma-dispensing HVAC filter.

12. The aroma-dispensing HVAC filter according to claim 11 wherein the fragrant odor exits the ventilation system via one or more air vents.

13. The aroma-dispensing HVAC filter according to claim 12 wherein the replaceable filter is cleaned and reused.

14. The aroma-dispensing HVAC filter according to claim 13 wherein the fragrance agent is reapplied to the replaceable filter from a container prior to reusing the aroma-dispensing HVAC filter.

* * * * *